United States Patent
Pfeiffer

(10) Patent No.: US 7,248,356 B2
(45) Date of Patent: Jul. 24, 2007

(54) CALIBRATION AID

(75) Inventor: Ulrich J. Pfeiffer, München (DE)

(73) Assignee: Pulsion Medical Systems AG, Munich (DE)

( * ) Notice: Subject to any disclaimer, the term of this patent is extended or adjusted under 35 U.S.C. 154(b) by 422 days.

(21) Appl. No.: 10/818,693

(22) Filed: Apr. 6, 2004

(65) Prior Publication Data

US 2005/0219524 A1    Oct. 6, 2005

(51) Int. Cl.
*G01J 1/10* (2006.01)
(52) U.S. Cl. .................................................. 356/243.1
(58) Field of Classification Search ............. 356/243.1; 283/108; 428/690; 436/530
See application file for complete search history.

(56) References Cited

U.S. PATENT DOCUMENTS

| 3,566,521 | A | * | 3/1971 | Conner ........................ 283/108 |
| 4,150,288 | A | * | 4/1979 | Inoue et al. .................... 378/50 |
| 4,157,895 | A | * | 6/1979 | Finlay et al. ................. 436/500 |
| 4,449,535 | A | | 5/1984 | Renault |
| 4,646,341 | A | * | 2/1987 | Finer et al. ................... 378/207 |
| 4,803,171 | A | * | 2/1989 | Baier et al. .................. 436/530 |
| 5,074,306 | A | | 12/1991 | Green et al. |
| 5,178,990 | A | | 1/1993 | Satake et al. |
| 5,403,706 | A | * | 4/1995 | Wilk et al. ....................... 435/4 |
| 5,552,288 | A | * | 9/1996 | Christensen et al. ......... 435/7.9 |
| 5,687,726 | A | | 11/1997 | Hoeft |
| 5,865,757 | A | | 2/1999 | Hoeft |
| 5,902,246 | A | * | 5/1999 | McHenry et al. ............ 600/476 |
| 6,223,069 | B1 | | 4/2001 | Pfeiffer et al. |
| 6,242,114 | B1 | * | 6/2001 | Yamasaki et al. ............ 428/690 |
| 6,631,286 | B2 | | 10/2003 | Pfeiffer et al. |
| 6,704,102 | B2 | * | 3/2004 | Roelke ..................... 356/243.1 |
| 6,927,062 | B2 | * | 8/2005 | Schoedel ........................ 436/8 |
| 2002/0133080 | A1 | * | 9/2002 | Apruzzese et al. ......... 600/477 |
| 2002/0183621 | A1 | | 12/2002 | Pfeiffer et al. |
| 2004/0196455 | A1 | * | 10/2004 | Ermantraut et al. ..... 356/243.1 |

FOREIGN PATENT DOCUMENTS

| DE | 32 10 593 | 10/1982 |
| DE | 41 30 931 | 3/1993 |
| DE | 43 25 529 | 11/1996 |

(Continued)

OTHER PUBLICATIONS

Anonymous: "Assay for billrubin" Research Disclosure, Kenneth Mason Publications, Hampshire, GB. vol. 161, No. 10. Sep. 1977, XP 007105054 ISSN: 0374-4353.

(Continued)

*Primary Examiner*—Layla G. Lauchman
*Assistant Examiner*—Jarreas Underwood
(74) *Attorney, Agent, or Firm*—Collard & Roe, P.C.

(57) ABSTRACT

A calibration aid may be assembled as follows. First, the standard reference substance is prepared by dissolving ICG dye and albumin protein in water. Then, the carrier sheet of fleece material is soaked therein and dried. After drying the carrier sheet, a thin well defined layer of protein bound dye is present at the surface of the fleece material. The carrier sheet and the backing sheet are laminated into a plastic card. For this, the plastic layers may be laminated tightly together in the framing region for example by welding or by use of adhesive. The plastic card is then sterilized and packed into a sealed package.

21 Claims, 1 Drawing Sheet

FOREIGN PATENT DOCUMENTS

| | | |
|---|---|---|
| DE | 100 59 070 | 2/2002 |
| EP | 1 210 906 | 11/2001 |
| EP | 1 254 630 | 4/2002 |
| WO | WO96/16594 | 6/1996 |
| WO | WO98/08434 | 3/1998 |

OTHER PUBLICATIONS

Krull I S et al: "Labeling reactions applicable to chromatography and electrophoresis of minute amounts of proteins" Journal of Chromaography B: Biomedical Sciences & Applications, Elsevier Schience Publishers, NL. vol. 699, No. 1-2, Oct. 10, 1997, pp. 173-208, XP 004094996, ISSN: 1570-0232 abstract, p. 198, par. 2.

European Search Report.

Derwent Abstract of DE 43 25 529.

Joseph Still, MD. et al. (1999) "Evaluation of the Circulation of Reconstructive Flaps using Laser-Induced Florescence of Indocyanine Green", Annals of Plastic Surgery 42:266-274.

Coleman, P.J., et al. "Hyaluronan secretion into the synovial cavity of rabbit knees and comparison with albumin turnover," Journal of Physiology (1997) London, UK, 503.3, pp. 645-656.

Hendradi, Esti, et al. "Effect of Mixed Micelle Formulations Including Terpenes on the Transdermal Delivery of Diclofenac," Biol. Pharm. Bull 26 (12), 2003, Tokyo, Japan, pp. 1739-1743.

* cited by examiner

CALIBRATION AID

BACKGROUND OF THE INVENTION

1. Field of the Invention

The present invention refers to a calibration aid for fluorescence measurement applications.

2. The Prior Art

An important field of application of fluorescence measurements is the field of non-invasive tissue perfusion quantification of a patient. A non invasive tissue perfusion imaging and quantification system is described in EP 1 210 906 A2. The patient is monitored with a digital camera while injecting indocyanine green (ICG, a fluorescent dye with an absorption maximum in the near infrared range) and irradiating the tissue of interest using a radiation source emitting radiation in the near infrared range. From the fluorescence signal of the tissue of interest (i.e. the light emitted by the fluorescent dye present in the blood flowing through the tissue) the perfusion state of the tissue can be determined using appropriate algorithms, such as disclosed in EP 1 210 906 A2. Equipment for intraoperative use of ICG measurements for determining tissue perfusion is further disclosed in DE 10059070 C1.

Advantageously, an external fluorescence standard is used when performing the measurements. It is placed next to the tissue of interest and, when irradiated, emits a constant and defined fluorescence signal which is recorded together with the fluorescence signal of the tissue of interest.

The use of a fluorescence standard allows to directly compare different measurements and to normalize measurement results based on the defined signal intensity of the fluorescence standard. It further allows compensating changes in the measurement conditions during a measurement (such as change in intensity of ambient light, change of exposure parameters of the camera or change of parameters of the radiation).

For reference purposes as described above, pure dry ICG dye is usually dissolved in water or methanol immediately before use. With this liquid sample an in vitro fluorescence measurement can be performed as described above. However, this practice is time consuming. Since ICG is not stable when exposed to air humidity and light, the reference standard must be prepared immediately before use, which is a major disadvantage when used in connection with urgent surgery. Moreover, the absorption and fluorescence properties of such pure dissolved standard samples are not equal to the properties of the protein bound dye after injection to a patient, e.g. the absorption maximum is shifted from 780 nm to 805 nm.

It is also not possible to use pure dry ICG dye for reference purposes as described above, since pure ICG powder also exhibits absorption and fluorescence properties different from dissolved ICG. Further, dry ICG may alter its properties due to ambient humidity.

SUMMARY OF THE INVENTION

Therefore, it is an object of the present invention to provide an easy to use ICG reference standard which is long time stable and does not need special preparation before use. Further, it is an object of the present invention to provide a method for producing such a reference standard.

According to one aspect of the present invention, the object is achieved by a calibration aid including a porous carrier body having a front side and a back side and a dry reference standard substance adhering to at least part of the surface of the carrier sheet. The reference standard substance includes albumin protein and a fluorescent dye. The calibration aid can be used as an external reference standard as described above. Preferred embodiments of the calibration aid may be designed as discussed below.

According to a particularly advantageous embodiment of the present invention, a calibration aid is enclosed in packaging material keeping it sterile before actual use as a disposable. Such a calibration kit includes a calibration aid whose complete outer surface is sterile and packaging material enclosing the calibration aid and configured to keep the outer surface of the calibration aid sterile. The calibration kit may be stored for longer periods of time without imposing on the patient the risk of an infection.

A calibration aid, or calibration kit, respectively, of the type described herein may be used together with commercially available angiography systems such as the IC-VIEW (trademark) system by Pulsion Medical Systems AG or similar systems. According to the present invention, a calibration aid as described herein can also be used as a fluorescence or absorption standard for use with other methods using injected indicator dyes.

According to the present invention, a calibration aid of the type mentioned can be manufactured using a method in which a porous carrier body having a front side and a back side is provided, a fluorescent dye is dissolved in a hydrophilic solvent to form a solution, the solution is applied onto the carrier body, and the carrier body is dried in order to remove the hydrophilic solvent from the carrier body. Preferred embodiments of this method may be designed as discussed below.

While in most embodiments the porous carrier body is flat and preferably made of textile sheet material (woven or non-woven), the porous carrier body may include sponge-like material, a zeolite bulk, sintered material of various types or other porous materials. Generally, a high volume specific surface area of the carrier body, preferably above 40 000 [1/m], more preferably above 200 000 [1/m], will be advantageous in connection with the present invention, and further the carrier body material has preferably a porosity of above 80%.

According to another aspect of the present invention, the calibration aid described above is used in a method for determining the blood flow in a tissue of interest of a living being, which may preferably be carried out as described in EP 1 210 906 A2 (U.S. Pat. No. 6,631,286) incorporated herein by reference.

BRIEF DESCRIPTION OF THE DRAWINGS

In the following, the invention is described, by way of non-limiting example, with reference to the accompanying schematic drawings, which are not to scale. It should be understood, however, that the drawings are designed for the purpose of illustration only and not as a definition of the limits of the invention.

In the drawings.

DETAILED DESCRIPTION OF PREFERRED EMBODIMENTS

Figure 1:
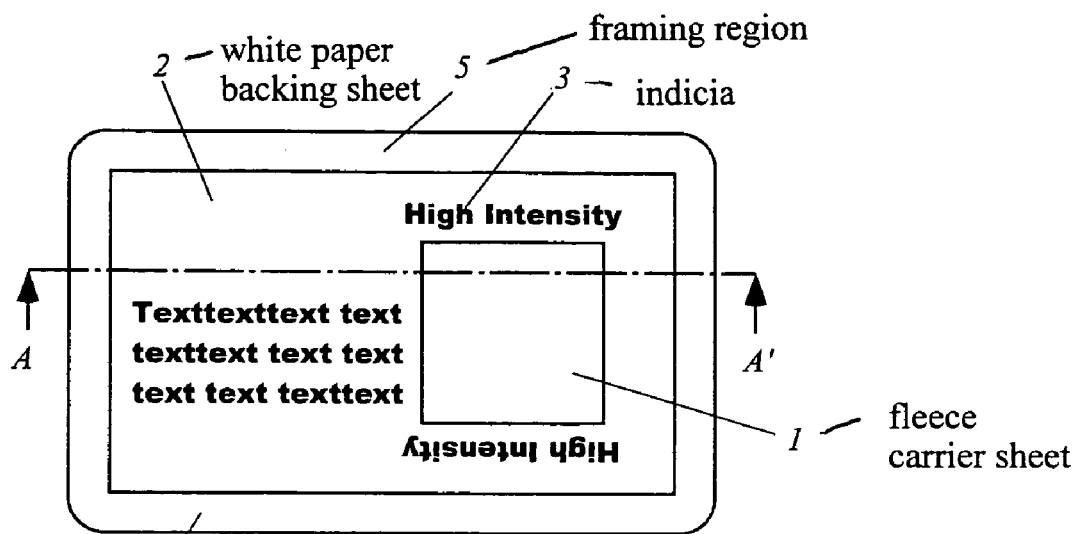
FIG. 1 shows a plan view of the front side of a calibration aid according to the present invention.
Figure 2:
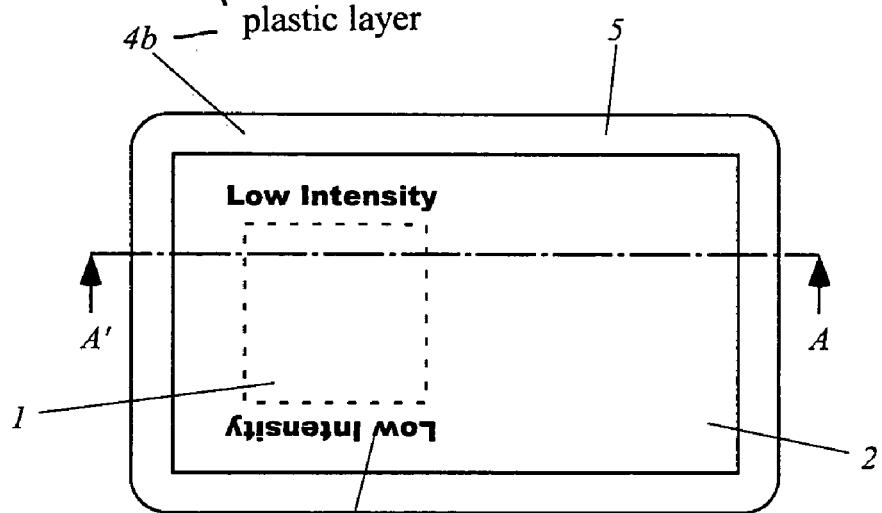
FIG. 2 shows a plan view of the back side of the calibration aid of FIG. 1.
Figure 3:
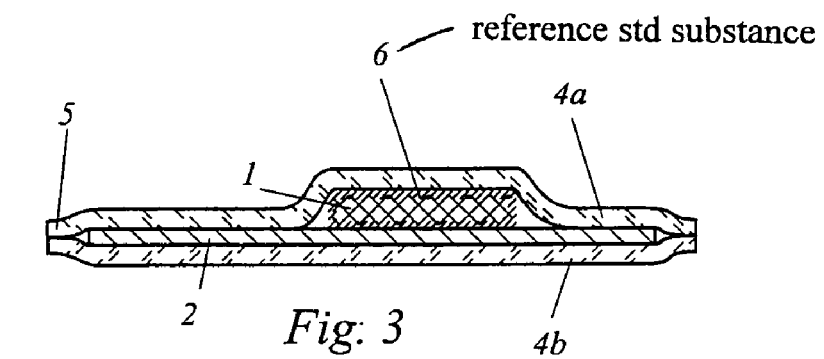
FIG. 3 shows a cross sectional view of the calibration aid of FIGS. 1 and 2 with a section plane orthogonal to the drawing plane of FIGS. 1 and 2, with the section plane being indicated by the broken line A-A' in FIGS. 1 and 2. The thickness of the individual layers is magnified by a large factor for illustrative purposes.

The calibration aid depicted in FIGS. 1-3 is designed as an easy to handle card-like object and includes a fleece carrier sheet 1, a white paper backing sheet 2 with indicia 3 printed thereon, and two transparent plastic layers 4a, 4b, laminated tightly together in the framing region 5. Preferably, the calibration aid is provided as a disposable sterile product, packed as a single device in a Tyvek® covered blister bag or other packaging material capable of preventing the outer surface of the calibration aid from being contaminated. Tyvek® is a polyolefin material available from E.I. Du Pont de Nemours & Co. of Wilmington, Del.

Fleece carrier sheet 1 may be made up of polyvinyl-alcohol fibers that are cross-linked with the help of a chemical agent. Fleece products of this type are available, for example, from Freudenberg Hauhaltsprodukte KG. Carrier sheet 1 is laden with a reference standard substance 6 including albumin protein and ICG fluorescent dye.

White paper backing sheet 2 extends beyond fleece carrier sheet 1. Commercially available paper of 80 grams per square meter is, among others, a suitable material for backing sheet 2. However, backing sheet 2 may also be made up of a plastic material. Preferably, backing sheet 2 has a certain degree of transparency for both electromagnetic radiation in the spectral range exciting reference standard substance 6 to fluoresce and the light emitted due to fluorescence. Thus, the calibration aid can be used as a high intensity standard when irradiated and viewed from the front side and as a low intensity standard when irradiated and viewed from the back side: By turning the plastic card, backing sheet 2 will attenuate the optical intensity, providing a second reference intensity level.

Indicia 3 may include instruction notes and other identification means. Therefore, the used reference standard may easily be documented by the camera also applied for fluorescence measurements.

Polyvinylchloride (PVC) film, such as commercially available from Klöckner Pentaplast (e.g. Pentafood LM 176), is a material suitable for transparent plastic layers 4a, 4b, but other materials capable of acting as a barrier against water diffusion due to ambient humidity may also be used. Because reference standard substance 6 is thus prevented from exposure to moisture, it is long-time stable. Because the dye of reference standard substance 6 is protein bound, the optical properties are similar to the properties of the dye when applied to a patient.

The calibration aid may be assembled as follows.

First, standard reference substance 6 is prepared by dissolving ICG dye and albumin protein in water. Then, carrier sheet 1 is soaked therein and dried. After drying carrier sheet 1, a thin well defined layer of protein bound dye is present at the surface of the fleece material. Carrier sheet 1 and backing sheet 2 are laminated into a plastic card. For this, plastic layers 4a, 4b may be laminated tightly together in framing region 5 for example by welding or by use of adhesive.

The plastic card is then sterilized and packed into a sealed package.

Since the calibration aid is sterile, it can be used intraoperatively. However, the calibration aid should not be placed on the tissue itself to prevent interference of the fluorescence signal emitted by the tissue with the fluorescence signal emitted by reference standard substance 6. Typically the calibration aid should be placed near the tissue of interest (e.g. on the operating table close to the patient). In cases where it is not possible to place the calibration aid beside the patient, because the standard would be too far away from the tissue of interest, the tissue has first to be covered by a material which is opaque for near-infrared light (e.g. an opaque sterile drape or abdominal pad) and the calibration aid has then to be placed on this opaque material.

The calibration aid is intended for single use during a fluorescence measurement (duration of the measurement typically about 8 minutes) and has to be discarded after the measurement.

While at least one embodiment of the present invention have been shown and described, it is to be understood that many changes and modifications may be made thereunto without departing from the spirit and scope of the invention as defined in the appended claims.

What is claimed is:

1. A calibration aid for fluorescence measurement applications, said calibration aid comprising
    (a) a porous carrier body having a front side and a backside;
    (b) a dry reference standard substance adhering to at least part of the surface of said carrier body, said reference standard substance comprising albumin protein and a fluorescent dye; and
    (c) a backing sheet covering the backside of said carrier body, said backing sheet having a degree of transparency for both electro-magnetic radiation in a spectral range exciting the fluorescent dye to fluoresce and a light emitted due to fluorescence of the fluorescent dye such that the calibration aid will exhibit high intensity of fluorescence when irradiated and viewed at the front side and a low intensity of fluorescence when irradiated and viewed at the backside.

2. The calibration aid according to claim 1, wherein said fluorescent dye comprises indocyanine green.

3. The calibration aid according to claim 1, wherein said carrier body is a textile carrier sheet.

4. The calibration aid according to claim 3, wherein said textile carrier sheet comprises a fleece material.

5. The calibration aid according to claim 4, wherein said textile carrier sheet comprises polyvinyl alcohol fibers.

6. The calibration aid according to claim 1, wherein said backing sheet is arranged to laterally extend beyond said carrier body in at least one direction.

7. The calibration aid according to claim 1, wherein said backing sheet has indicia printed thereon.

8. The calibration aid according to claim 1, wherein said backing sheet includes paper material.

9. The calibration aid according to claim 1, further comprising at least one transparent plastic layer configured to serve as a humidity barrier for protection of said carrier body against humidity.

10. The calibration aid according to claim 9, wherein said plastic layer includes polyvinylchloride (PVC) film material.

11. The calibration aid according to claim 1, wherein the front side of said carrier body extends over an area of between 100 and 5000 square millimeters.

12. The calibration aid according to claim 1, wherein the complete outer surface of said calibration aid is sterile.

13. A calibration kit comprising a calibration aid according to claim 12 and packaging material enclosing said calibration aid and configured to keep the outer surface of said calibration aid sterile.

14. A method for producing a calibration aid for fluorescence measurement applications, comprising the steps of
    (a) providing a porous carrier body having a front side and a backside;
    (b) dissolving a fluorescent dye in a hydrophilic solvent to form a solution;
    (c) applying said solution onto said carrier body;

(d) drying said carrier body in order to remove said hydrophilic solvent from said carrier body; and (e) covering the backside of said carrier body with a backing sheet, said backing sheet having a degree of transparency for both electro-magnetic radiation in a spectral range exciting the fluorescence dye to fluoresce and a light emitted due to fluorescence of the fluorescent dye such that the calibration aid will exhibit high intensity of fluorescence when irradiated and viewed at the front side and a low intensity of fluorescence when irradiated and viewed at the backside.

15. The method according to claim 14, further comprising the step of dissolving albumin protein in said hydrophilic solvent prior to applying said solution onto said carrier body.

16. The method according to claim 14, wherein said hydrophilic solvent comprises water.

17. The method according to claim 14, wherein the backside of said carrier body is covered with said backing sheet such that the backing sheet laterally extends beyond said carrier body in at least one direction.

18. The method according to claim 14, further comprising the step of printing indicia onto said backing sheet prior to the step of covering the backside of said carrier body with said backing sheet.

19. The method according to claim 14, further comprising the step of laminating together said carrier body with at least two layers of a transparent plastic material to form a card like object.

20. The method according to claim 14, further comprising the step of sterilizing the outer surface of said calibration aid.

21. The method for determining the blood flow in a tissue of interest of a living being using a calibration aid as defined in claim 1, said method including the steps of (a) injecting fluorescent dye of the same species as the fluorescent dye comprised in the reference standard substance of said calibration aid;

(b) placing said calibration aid in a distance from said tissue of interest said distance being such that both said tissue of interest and said calibration aid can be irradiated simultaneously by a radiation source and viewed simultaneously by a digital camera; and (c) simultaneously irradiating said tissue of interest and said calibration aid causing said fluorescent dye to fluoresce.

* * * * *